United States Patent [19]

Darling, Jr.

[11] Patent Number: 5,730,730
[45] Date of Patent: Mar. 24, 1998

[54] LIQUID FLOW RATE CONTROL DEVICE

[76] Inventor: Phillip H. Darling, Jr., 5591 Rockledge Dr., Buena Park, Calif. 90621

[21] Appl. No.: 674,552

[22] Filed: Jul. 1, 1996

Related U.S. Application Data

[60] Provisional application No. 60/004,634, Sep. 29, 1995.

[51] Int. Cl.$^6$ ..................................................... A61M 5/14
[52] U.S. Cl. ........................... 604/246; 604/247; 604/254
[58] Field of Search ................................. 604/245, 246, 604/247, 249, 254

[56] References Cited

U.S. PATENT DOCUMENTS

| | | |
|---|---|---|
| 1,235,316 | 7/1917 | Henderson . |
| 2,374,076 | 4/1945 | Burckhardt . |
| 2,665,706 | 1/1954 | Hansen . |
| 2,850,211 | 9/1958 | Fernandez . |
| 2,854,992 | 10/1958 | Hewitt . |
| 3,001,397 | 9/1961 | Leonard . |
| 3,034,504 | 5/1962 | Winsor . |
| 3,123,094 | 3/1964 | Toschkoff . |
| 3,216,418 | 11/1965 | Scislowicz . |
| 3,216,419 | 11/1965 | Scislowicz . |
| 3,323,550 | 6/1967 | Lee . |
| 3,468,308 | 9/1969 | Bierman . |
| 3,563,090 | 2/1971 | Deltour . |
| 3,566,897 | 3/1971 | Collier . |
| 3,581,754 | 6/1971 | Adams . |
| 3,587,313 | 6/1971 | Smith . |
| 3,731,681 | 5/1973 | Blackshear . |
| 3,738,361 | 6/1973 | Price . |
| 3,744,492 | 7/1973 | Leibinsohn . |
| 3,890,968 | 6/1975 | Pierce . |
| 3,929,157 | 12/1975 | Serur . |
| 3,931,818 | 1/1976 | Goldowsky ........................ 128/214 |
| 3,989,043 | 11/1976 | Dimeff .............................. 128/214 |
| 4,043,332 | 8/1977 | Metcalf . |
| 4,142,523 | 3/1979 | Stegeman . |
| 4,143,659 | 3/1979 | Biedermann . |
| 4,186,740 | 2/1980 | Guerra . |
| 4,187,847 | 2/1980 | Loeser . |
| 4,191,208 | 3/1980 | Mylander . |
| 4,207,871 | 6/1980 | Jenksins . |
| 4,217,993 | 8/1980 | Jess . |
| 4,265,240 | 5/1981 | Jenkins . |
| 4,340,050 | 7/1982 | Noiles . |
| 4,375,813 | 3/1983 | Hessel . |
| 4,405,000 | 9/1983 | Fuller . |
| 4,436,090 | 3/1984 | Darling . |
| 4,474,574 | 10/1984 | Wolfe . |
| 4,496,351 | 1/1985 | Hillel . |

(List continued on next page.)

FOREIGN PATENT DOCUMENTS

| | | | |
|---|---|---|---|
| 7524659 | 8/1974 | France ................................ 604/254 |
| 8400287 | 8/1985 | Netherlands ......................... 604/246 |

*Primary Examiner*—Michael Buiz
*Assistant Examiner*—Julian W. Woo
*Attorney, Agent, or Firm*—Howard R. Lambert

[57] ABSTRACT

A fluid flow rate control device, especially adapted for controlling the flow of IV fluid to a patient, comprises a first vented fluid chamber having an upper fluid inlet end with a hollow spike which enables fluid connection with a conventional fluid container. A free floating float valve in the first chamber blocks the flow of fluid into the first chamber from the fluid container according to whether or not the fluid level in the first chamber is at a preestablished fluid level, thereby providing a constant pressure head regardless of fluid level in the fluid container. A lower end of the first chamber is connected, through a flow regulator, such as a screw-type valve, to an upper inlet end of a second, vented, drip chamber, the lower end of which is adapted for connection to a discharge tube, such as an IV tube. A second, free floating float valve in the second chamber blocks the flow of fluid from the second chamber into the discharge tube when the fluid level in the second chamber is at or below a preestablished minimum level and blocks flow of fluid into the second chamber when the fluid level in the second chamber reaches a preestablished maximum level.

28 Claims, 3 Drawing Sheets

U.S. PATENT DOCUMENTS

| | | |
|---|---|---|
| 4,515,588 | 5/1985 | Amenoolia . |
| 4,522,228 | 6/1985 | Campau . |
| 4,588,396 | 5/1986 | Stroebel . |
| 4,613,325 | 9/1986 | Abrams . |
| 4,789,000 | 12/1988 | Aslanian . |
| 4,802,506 | 2/1989 | Aslanian . |
| 4,807,660 | 2/1989 | Aslanian . |
| 4,857,048 | 8/1989 | Simons . |
| 4,863,437 | 9/1989 | Clarke . |
| 4,931,050 | 6/1990 | Idriss . |
| 4,976,687 | 12/1990 | Martin . |
| 5,019,047 | 5/1991 | Kriesel . |
| 5,033,714 | 7/1991 | Winchell et al. . |
| 5,104,750 | 4/1992 | Winchell et al. . |

LIQUID FLOW RATE CONTROL DEVICE

BACKGROUND OF THE INVENTION

This application claims the benefit of U.S. provisional application Ser. No. 60/004634, filed Sep. 29, 1995.

FIELD OF THE INVENTION

The present invention relates generally to apparatus for controlling flow rates of liquids and, more particularly, to apparatus for maintaining accurate, precise and stable liquid flow rates in medical liquid delivery systems, such as intravenous (IV) fluid delivery systems.

BACKGROUND DISCUSSION

Many applications exist in which the precisely-controlled flow of small quantities of liquid materials is essential. One particularly critical example of such applications is the required precise delivery of controlled amounts of intravenous (IV) liquids to patients in hospitals, clinics, or in the field.

Gravity-driven IV liquid delivery systems or devices known to the present inventor utilize variable orifice flow control valves to control the flow rate of fluids to a patient undergoing treatment. Such known valves require a constant pressure drop, $\Delta P$, across the orifice to maintain a stable, accurate and precise flow rate of fluid into patients to which the systems or devices are connected.

Some of these known flow control systems or devices utilize one or more fixed orifices and adjust the pressure drop, $\Delta P$, across the orifice(s) to set the fluid flow rate. This pressure drop (the absolute sum of the positive and negative pressure) across the orifice(s) calibrated for a liquid of known viscosity and density determines the instantaneous fluid flow rate through the orifice(s).

Many known variable and fixed orifice fluid flow control systems attempt to circumvent or accommodate the normal decrease in positive fluid head pressure as the supply liquid level drops as, for example, liquid is drained from an IV bottle, and also variations in negative or suction pressure in the patient delivery line, as may, for example, be caused by patient movement or changes in the patient's venous pressure.

Variable orifice flow control valves of some known IV flow control devices are marked with flow rates that appear to assume an average pressure drop, $\Delta P$, across the orifice, with no control of supply head pressure or patient line suction. For example, the fluid flow control valves disclosed in U.S. Pat. Nos. 4,789,000; 4,802,506 and 4,807,660 are considered representative of this type device. Instructions provided with commercial versions of the just-mentioned type of IV flow control devices caution users initially to count the number of liquid drops falling through an associated drip chamber in a prescribed period of time to establish an accurate flow rate, and thereafter to adjust the valve frequently to maintain a relatively constant liquid delivery rate as the supply liquid head and/or the patient line pressures changes.

Other known IV flow rate control systems, such as those disclosed in U.S. Pat. Nos. 3,929,157; 4,340,050 and 4,588, 396, disclose or suggest controlling fluid head pressure by transferring liquid from a primary liquid supply source into a secondary vessel in which the level is held constant and independent of the decreasing head pressure of the primary liquid source as it empties.

Other examples of known IV devices are disclosed in U.S. Pat. No. 3,929,157. These particular patents disclose IV devices in which a tube connects a rigid supply source to a secondary chamber for head pressure control. Liquid flows under gravity from the supply source into the secondary chamber until the bottom of the tube is covered. At that point air can no longer pass up the tube to displace the in-flowing liquid and flow stops. The region above the liquid in the secondary chamber is connected to the atmosphere (that is, the region is at atmospheric pressure), so there is no coupling through the air between the supply head pressure and the head pressure in the chamber.

The head pressure on a fixed outlet orifice located in the bottom of the secondary chamber determines the rate of flow, which may be adjusted by sliding the secondary chamber up or down on the tube from the supply source, thereby adjusting the head pressure of the liquid in the secondary chamber. A liquid collection chamber below the orifice collects the liquid and a flexible tube conducts the liquid from the collection chamber to a patient. This collection chamber is also vented to atmosphere so that changes in the liquid height in the patient line or changes in venous back pressure are uncoupled from the orifice and will have no effect on the flow rate through the orifice.

U.S. Pat. No. 4,340,050 discloses the use of a collapsible bag for the supply source. The bag discharges liquid into a liquid-receiving chamber which is vented to the atmosphere. A float-type valve is pivotally mounted in the liquid-receiving chamber for maintaining a constant liquid level. As disclosed, a second chamber, having fixed orifices at various heights and which is fluidly connected to the liquid-receiving chamber, can be moved up and down relative to the liquid-receiving chamber to vary the head pressure on the orifices. Liquid passing through the orifices collects in the bottom of the second chamber and is conducted to a patient through a flexible IV tube. This second chamber is vented to the atmosphere above the liquid on both sides of the orifices, thereby uncoupling the orifices from any pressure changes in the IV line connected to the patient.

In another example of the known IV flow control art, U.S. Pat. No. 4,588,396 discloses the use of a tube which connects a rigid supply source to a liquid-receiving chamber in which a constant liquid level is maintained in the manner disclosed in above-mentioned U.S. Pat. No. 3,929,157. The air above the liquid in the receiving chamber, which is the source of displacement air in the supply vessel, is vented to atmosphere through a metering valve which is used for flow rate control, instead of an orifice being used in the IV liquid path. Liquid is disclosed as flowing out of this collection chamber through a sealed drip chamber which is connected to a patient delivery line. It appears, however, that changes in the height of the liquid in the patient line will couple through the air in the sealed drip chamber to the liquid in the collection chamber and affect the flow rate through the system.

Other known IV flow rate control systems, such as are disclosed in U.S. Pat. Nos. 4,142,523; 4,186,740; 4,515,588 and 4,863,437, use a diaphragm or collapsible chamber which adjusts a flow control orifice or passage to minimize flow rate changes caused by supply head pressure and patient delivery line pressure variations. As far as the present inventor is aware, however, none of such disclosed IV devices isolate the flow control element from both the supply head and patient line pressure variations.

By way of a still further example, U.S. Pat. No. 4,613,325 discloses an IV flow rate control system that amplifies and uses a velocity dependent pressure drop across a restriction in the flow path to modulate the size of an upstream variable orifice flow control. There does not, however, appear to be disclosed any means for isolating the flow restriction from supply head or patient line pressure variations.

Further examples of known IV flow control devices are disclosed in U.S. Pat. Nos. 5,014,750 and 5,033,714. These patents disclose a pressurized constant pressure liquid supply that is fed through an adjustable flow restricter into a patient delivery line, the entire IV system being worn by the patient. However, since the system is tied to the patient, little variation would be expected in patient line pressure except that caused by venous blood pressure.

Many of the known IV flow rate control devices that attempt to compensate for changes in supply head pressure and patient line pressure are expensive and complex, and the range of pressure compensation before a nurse must reset the flow rate is considered by the present inventor to be limited, particularly, since in a "worst case" situation a patient's line suction on the flow control orifice can, depending, for example, on the patient's position (e.g., standing, sitting or lying) increase by 30 to 40 cm of water, possibly doubling the pressure drop across the orifice.

An important need, therefore, still exists in the medical field for an improved, simple, reliable and relatively low-cost, gravity-driven IV system that delivers an accurate, precise and stable flow rate of medicinal liquid to patients, in bed or ambulatory, in hospital, home, field or transport settings. It is, therefore, a principle objective of the present invention to provide such an improved IV system.

SUMMARY OF THE INVENTION

In accordance with the present invention, there is provided a gravity flow fluid flow regulating device with constant fluid head provision that is particularly for regulating the flow of fluids, such as IV fluids, from a fluid source into a patient's body. The flow regulating device comprises a first, constant fluid head chamber having an upper fluid inlet end region and a lower, fluid outlet region. Included is a second, drip, chamber having an upper fluid inlet end region and a lower, fluid outlet end region, the lower fluid outlet end region being configured for having attached thereto a fluid delivery tube, such as a conventional IV fluid delivery tube for providing IV fluid into a patient's body.

Further comprising the present invention are fluid flow regulating means connected in fluid flow relationship between the fluid outlet end region of the first chamber and the fluid inlet end region of the second chamber, the regulating means being configured for regulating the gravity flow of fluid from the first chamber into the second chamber.

Further included are means enabling a fluid-flow connection between the fluid inlet end region of the first chamber and a lower, discharge region of a fluid source, such as a source of IV fluid that may be either open or closed to ambient pressure.

Still further included in the present flow control device are first, upper, fluid level control means disposed in the first chamber for causing, when the connecting means connect the first chamber to a preexisting source of fluid for receiving a flow of fluid therefrom, a preestablished fluid level to be substantially maintained in the first chamber as the fluid level in the source decreases.

In accordance with a preferred embodiment of the invention, the first, upper, fluid level control means include an inlet orifice at the fluid inlet end region of the first chamber and a first, upper, float valve disposed in a free-floating relationship inside the first chamber. The first, upper, free-floating valve is configured for blocking the inlet orifice to stop the gravity flow of fluid through the orifice from a connected source of fluid when the fluid level in the first chamber is at the preestablished level and for unblocking the inlet orifice to permit a gravity flow of fluid through the orifice from the fluid source when the fluid level in the first chamber falls below the preestablished level.

Also included in the present flow control device are first venting means located at an upper region of the first chamber above the preestablished fluid level therein for venting the first chamber to ambient surrounding pressure and second venting means located at an upper region of the second chamber for venting the second chamber to ambient surrounding pressure.

At least a side wall region of the second chamber is constructed of a transparent material so that a rate of fluid dripping through the second chamber can be observed by a user of the device.

Further, according to a preferred embodiment, the fluid flow regulating means comprise a valve body having a rotatably-mounted valve stem for incremental rotational movement between a first, fully-closed position which blocks the gravity flow of fluid from the first chamber into the second chamber and a second, fully-open position in which the gravity flow of fluid from the first chamber into the second chamber is at a maximum flow. The valve stem is disposed in the valve body for being manually set at any selected rotational position between the first and second positions so as to thereby enable a user of the device to selectively control the gravity flow of fluid from the first chamber into the second chamber. An indicator dial calibrated with respect to rotational positions of the valve stem may be provided for enabling a user to read fluid flow rates from the first chamber into the second chamber associated with different rotational positions of the valve stem.

A second, lower, flow control means comprises a second, lower valve that is disposed in free-floating relationship inside the second chamber for closing the lower, fluid outlet end region when fluid in the second chamber falls to a preestablished lower level to prevent the inclusion of air from the outlet region of the second chamber, for example, into the fluid conduit to a patient's body and for alternatively closing the fluid inlet to the second chamber when the fluid in the second chamber rises to a preestablished upper level.

In a variation of the fluid flow control device, the fluid flow regulating means of the flow control device comprise a flexible fluid conduit connected in fluid flow relationship between the outlet end region of the first chamber and the fluid inlet end region of the second chamber. In such configuration, means are included for selectively controlling the vertical distance between the preestablished fluid level in the first chamber and the fluid inlet region of the second chamber.

There is accordingly provided a fluid flow control device, particularly for use in an IV supply system, which, as an illustration, provides a constant fluid head as the fluid level in a source of IV fluid to which the device is connected decreases as the fluid is introduced into through the device into a patient's body.

BRIEF DESCRIPTION OF THE DRAWINGS:

The present invention can be more readily understood by a consideration of the following detailed description when taken in conjunction with the accompanying drawings, in which.

In the various FIGS. identical elements and features are given the same reference number and similar elements and features may be given the original reference number followed by an "a" as will be clear from the following description.

Figure 1:
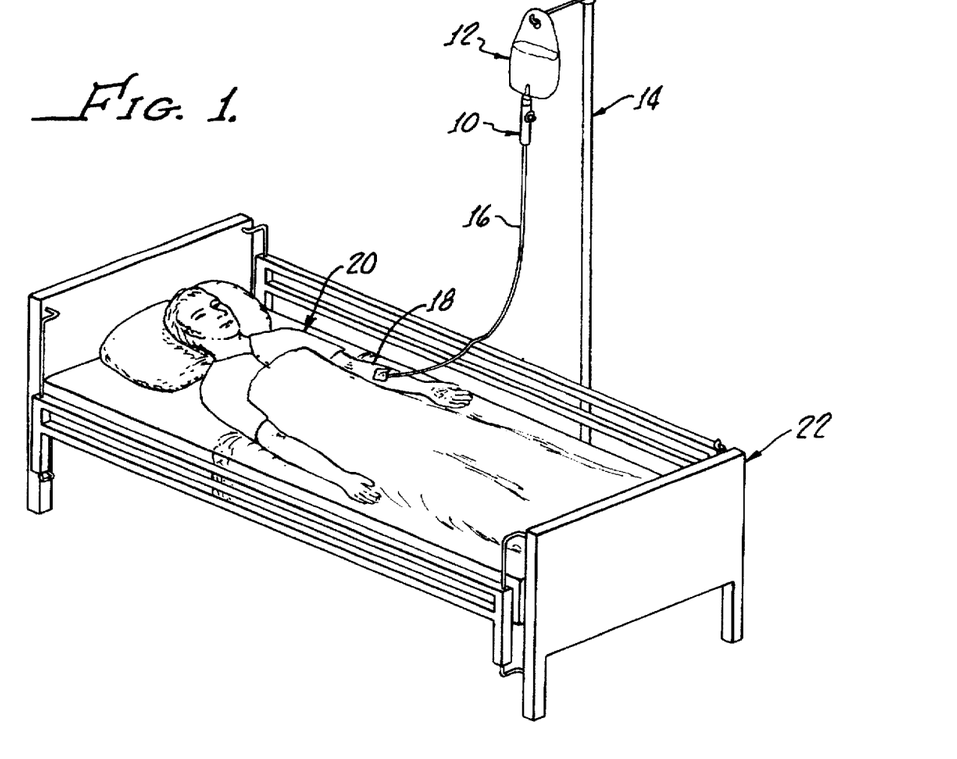
FIG. 1 is a pictorial drawing which illustrates a typical manner in which the flow rate control device of the present invention may be used to advantage, there being shown the device connected to a exemplary IV solution or fluid container and showing the output of the device being connected, through an IV tube, into the arm of a reclining patient.

DETAILED DESCRIPTION OF THE INVENTION:

In FIG. 1 there is depicted a flow rate control device or system 10, in accordance with the present invention. Device or system 10 is shown, by way of illustrative example, and as more particularly described below, connected, at an upper inlet end region, in fluid receiving relationship to a conventional IV supply source of container 12, which is depicted as being supported at an elevated level by a conventional IV stand 14. A lower end region of device 10 is shown connected in a fluid discharging relationship to the upper end of a conventional IV fluid supply conduit or tube 16 which has a lower end connected to a canula (not shown) inserted into an arm 18 of a patient 20 shown reclining on a hospital bed 22.

Figure 2:
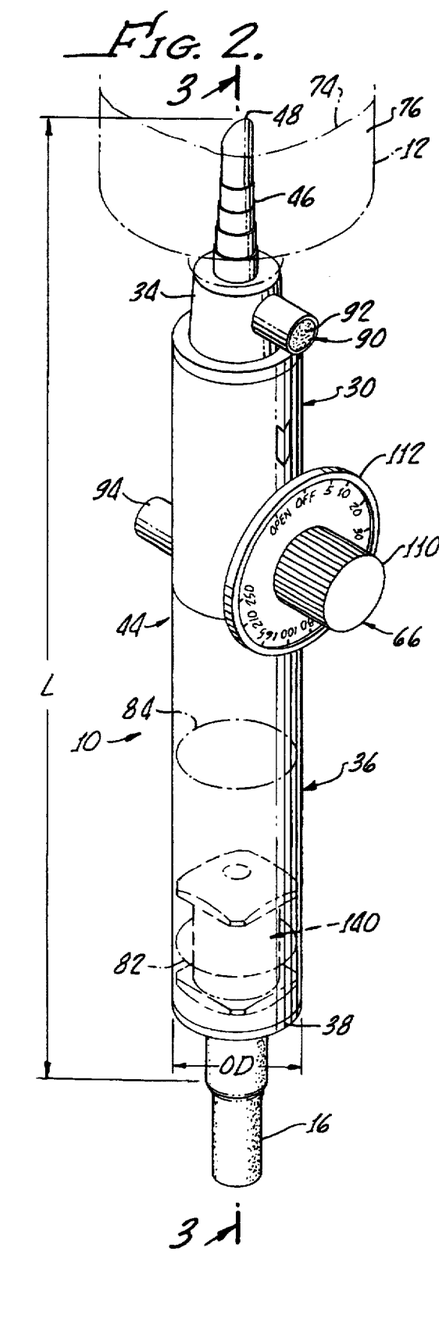
FIG. 2 is a partial perspective drawing of the flow rate control device of the present invention, showing the external configuration thereof and showing the upper, inlet end of the device connected to a lower region of an exemplary IV fluid container and showing the lower, output end of the device connected to an upper end region of a patient fluid delivery tube and showing a transparent drip chamber portion of the device.
Figure 3:
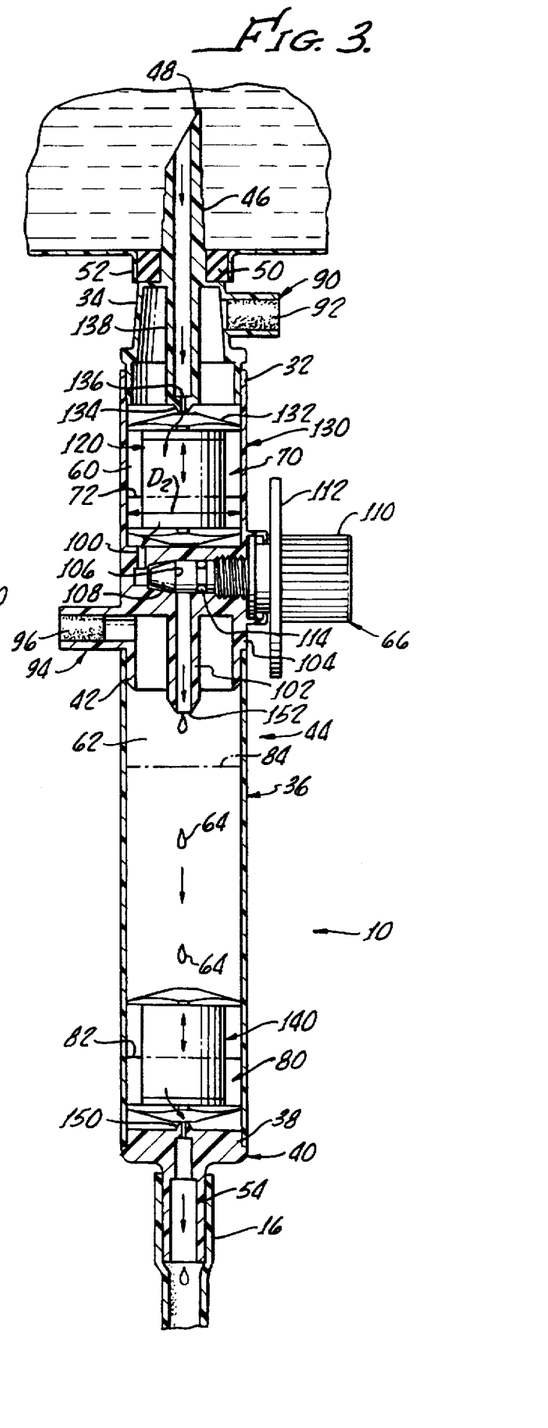
FIG. 3 is a longitudinal cross sectional view taken along line 3—3 of FIG. 2 showing the internal construction of the flow rate control device and showing a first, upper, free-floating float valve, a flow regulating valve and a second, lower, free-floating float valve for controlling and regulating fluid flow through the device.

As shown in FIGS. 2 and 3, and as more particularly described below, flow rate control device or system 10 is externally constructed of a generally tubular upper shell segment 30, having joined to an upper end thereof a lower region 32 of a hollow inlet member 34, and a tubular lower shell segment 36, having joined to a lower end thereof an upper end region 38 of a discharge member 40. A lower end region 42 of upper shell segment 30 is joined to the upper end of lower shell segment 36 so as to form a slender, vertically-elongated and substantially closed device body 44.

As best seen from FIG. 3, an upwardly-projecting end region 46 of inlet member 34 (which is preferably constructed from a medical-grade plastic) is formed in the shape of a slender, tapered, hollow spike having a relatively sharp, beveled upper end 48 which enables fluid-flow penetration of the inlet member through a seal or plug 50 at a lower, discharge end region 52 of fluid container 12 to thereby enable the gravity flow of fluid from the container into upper segment 30.

A downwardly-extending end region 54 of discharge member 40 is formed in slender tubular shape for receiving an upper end of tube or conduit 16 to enable fluid flow from device 10 into patient 20.

As further shown in FIG. 3, internal surfaces of upper shell segment 30 and inlet member 34 largely form or define a first, upper chamber 60, and internal surfaces of lower shell segment 36 and discharge member 40 largely form or define a second, lower chamber 62.

At least regions, and preferably all, of lower shell segment 36 are formed of a transparent material, (for example, medical grade plastic such as polystyrene), so that fluid flowing through lower chamber 62 in the form of droplets 64 can be viewed and counted by a user of device 10 to obtain and/or monitor the fluid flow rate (for example, in milliliters per hour) through the device.

Shown formed integrally in lower regions of upper shell segment 30 (and more particularly described below) are fluid flow regulating means 66 which regulate the gravity flow of fluid from first, upper chamber 60 into second, lower chamber 62, and consequently through device 10.

Also as more particularly described below, first, upper, fluid flow controlling means 70 are disposed in first, upper chamber 60 for maintaining a predetermined, uniform fluid level 72 in such chamber as a level 74 of fluid 76 (FIG. 2) in container 12 changes as fluid flows from the container into and through device 10. That is, upper fluid flow controlling means 70 provide a constant fluid pressure head in device 10 regardless of the changing pressure head in fluid container 12 as fluid is drawn therefrom.

Second, lower, fluid flow controlling means 80 are disposed in second, lower chamber 62 for stopping the flow of fluid from such chamber into tube 16 when the fluid level in such chamber falls below a predetermined minimum level 82 so as to prevent the introduction of air into fluid being discharged from device 10. Second, lower, fluid flow containing means 80 are also configured, relative to the height of second chamber 62 for shutting off the flow of fluid into the lower chamber from upper chamber 60 when the fluid level in the lower chamber reaches a preestablished maximum level 84 (shown in phantom lines, FIG. 3).

An upper vent tube 90 is connected through a side wall of upper member 34 to vent upper chamber 60 to atmosphere. A conventional micropore filter element 92 is installed in filter tube 90 to maintain sterility of the upper chamber. Similarly, a lower vent tube 94, having a micropore filter element 96 is connected through a lower, side wall region of upper shell segment 30 to vent lower chamber 62 to atmosphere while maintaining sterility of the chamber.

Flow regulating means 66, as depicted in FIG. 3, comprises a generally conventional, screw-type fluid flow regulating valve which includes flow respective upper and lower, vertical fluid channels 100 and 102 formed in a lower region 104 of upper shell section 30. Fluid channels 100 and 102, which enable the flow of fluid from upper chamber 60 into upper regions of lower chamber 62 are interrupted by a valve shaft 106 having a tapered flow control section 108.

An external control knob 110 connected to a proximal end of shaft 106 enables a user to rotate the shaft so that tapered section 108 is drawn to the right. This action opens, in varying degrees, the flow path between channels 100 and 102 so as to provide a variable cross section conduit enabling the regulation of fluid flow from upper chamber 60 into lower chamber 62, to the desired or required flow rate.

A fluid flow indicating scale 112 may be provided beneath knob 110 to indicate, according to the rotational position of the knob, the precise fluid flow rate through regulating means 66. However, the flow rate may be verified by a user by counting the rate at which fluid droplets 64 fall through second chamber 62. A conventional O-ring seal 114 is installed around valve stem 106 to prevent fluid leakage past the shaft and from device 10.

Figure 4:
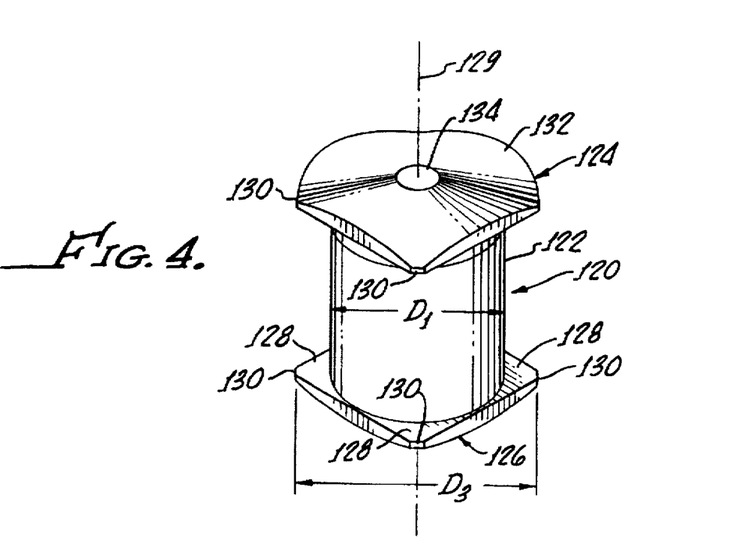
FIG. 4 is a partially cutaway perspective drawing of a representative one of the first and second free-floating float valves, showing the external configuration thereof with upper and lower end caps configured for having only minimal edge contact with their respective device chambers.

First, upper flow control means 70 comprises a buoyant first float valve 120 which is sized and configured for freely floating in a vertical direction inside of upper chamber 60. As best seen in FIG. 4, first float valve 120 comprises a light-weight, cylindrical plastic tubular body 122 having generally square, upper and lower end caps 124 and 126, respectively. The outer diameter, $D_1$, of body 122 is smaller than inner diameter, D, of upper chamber 60 (FIG. 3).

As shown for representative bottom end cap 126, all corners 128 thereof extend radially outwardly from body 122, in a symmetrical manner about a vertical axis 129 of valve 120, and terminate in short arcuate end or corner surfaces 130 which define a circle having a diameter, $D_3$, which is slightly smaller that the inside diameter, $D_2$, of upper chamber 60. Edge surfaces 130 function as guide surfaces making minimal contact with the inside of upper chamber 60 as valve 120 floats freely up and down, according to the fluid level in the chamber.

As shown in FIG. 4 for upper end cap 124, an upper surface 132 thereof is slightly convex and has a small flat circular central surface region 134 which functions as a flow-blocking surface when valve 120 floats upwardly in upper chamber 60 until such surface bears against, and blocks the gravity flow of fluid from a mating fluid orifice 136 at the lower end of a tubular downward extension 138 of spike 46 (FIG. 3).

Preferably, upper and lower valve end caps 124 and 126 are identical to one another and are joined to respective upper and lower ends of body 122 in a manner sealing first float valve 120 against fluid leaks which would affect buoyancy of the valve.

It is also preferable that second, lower flow controlling means 80 comprise a second, lower valve 140 which is identical in function, and also preferably in construction, to above-described first, upper valve 120. Lower valve 140 is free to float up and down in second chamber 62 between lower and upper preestablished fluid levels 82 and 84, respectively, according to the fluid level in the second chamber, and thereby opening and closing an outlet orifice or opening 150 at the bottom of the second chamber and an inlet orifice or opening 152 through which fluid is dropped into the second chamber.

By way of illustrative example (referring to FIG. 2), the overall length, L, of device 10 may be about 18 centimeters and the outside diameter, OD, of sections 30 and 36 may be about 2.5 centimeters, such that the combined volumes of first and second chambers 60 and 62 is about 45 milliliters. It can be appreciated that the constant fluid column height across flow control 66 is essential to the precision of fluid flow control provided by device 10.

Operation of Device 10

The operation of fluid flow controlling device 10 is readily apparent from the above description thereof in conjunction with associated FIGS. 1–4. Nevertheless, a brief summary of the operation of device 10 follows.

When constructed and assembled in the above-described manner, device 10 is ready for being operationally installed between fluid container 12 and fluid tube 16 into a patient 20 by inserting device spike 46 through container seal 50 and installing fluid tube 16 onto device bottom projection 54 (FIGS. 1–3).

Upon such installation (assuming that fluid is contained in container 12, that device 10 is hanging in a substantially vertical orientation as depicted in FIGS. 2 and 3, and that flow regulator valve 66 is closed) first float valve 120 will initially be resting at the bottom of first chamber 60 and second float valve 140 will be resting at the bottom of second chamber 62. As fluid flows into first chamber 60 from fluid container 12, the fluid level in the first chamber will rise, causing first float valve to float upwardly toward fluid inlet opening 136.

When the preestablished fluid level 72 is reached in first chamber 60, first float valve 120 will have floated to an elevation where upper surface region 134 of valve upper cap 124 blocks off further fluid flow into the first chamber. Flow regulator valve 66 is then opened slowly to establish the desired or required fluid flow rate from first chamber 60 into second chamber 62 (for example, by counting the number of droplets 64 falling through the second chamber over a given time interval). This flow of fluid from first chamber 60 into second chamber 62 causes the fluid level in the first chamber to fall, thereby causing first float valve 120 to float downwardly and open inlet opening 136 so that additional fluid can flow from container 12 into the first chamber until the preestablished fluid level is again reached and the first float valve again seals off fluid flow into the first chamber.

In this manner, an equilibrium situation is reached wherein as each drop of fluid flows from first chamber 60, through regulator valve 66, first float valve 120 floats down just a sufficient distance to permit a similar drop of fluid to be flowed from fluid container 12 into the first chamber before the first float valve floats back up and again shuts off the inflow of fluid from the fluid container.

Second float valve 140 in second chamber 62 functions in a reverse manner to meter fluid from the second chamber into tube 16 and on to patient 20. After initially being lifted upwardly by fluid received from first chamber 60 accumulating in lower regions of second chamber 62 to the preestablished minimum level, second float valve unblocks outlet opening 150 sufficiently to permit a drop equivalent of fluid to be discharged into tube 16. This causes a decrease in the fluid level in second chamber sufficient for second float valve to float down and reclose discharge opening 150 until the valve is relifted by a next drop of fluid dropping into the second chamber, such that each drop of fluid entering second chamber 62, a like volume is discharged therefrom into tube 16 and thence to patient 20.

If the flow of fluid from second chamber 62 into tube 16 is blocked in the tube or patient (the latter, for example, by a collapsed vein), fluid backs up in the second chamber until second valve 140 floats to the top of the chamber and cuts off the inflow of fluid until the blockage in the tube or patient is cleared.

With respect to the foregoing operation, it will be appreciated that the various preestablished fluid levels 72, 82 and 84 are selected in combination with the characteristics of the first and second float valves to cause the described operation.

Figures 5, 6, 7:
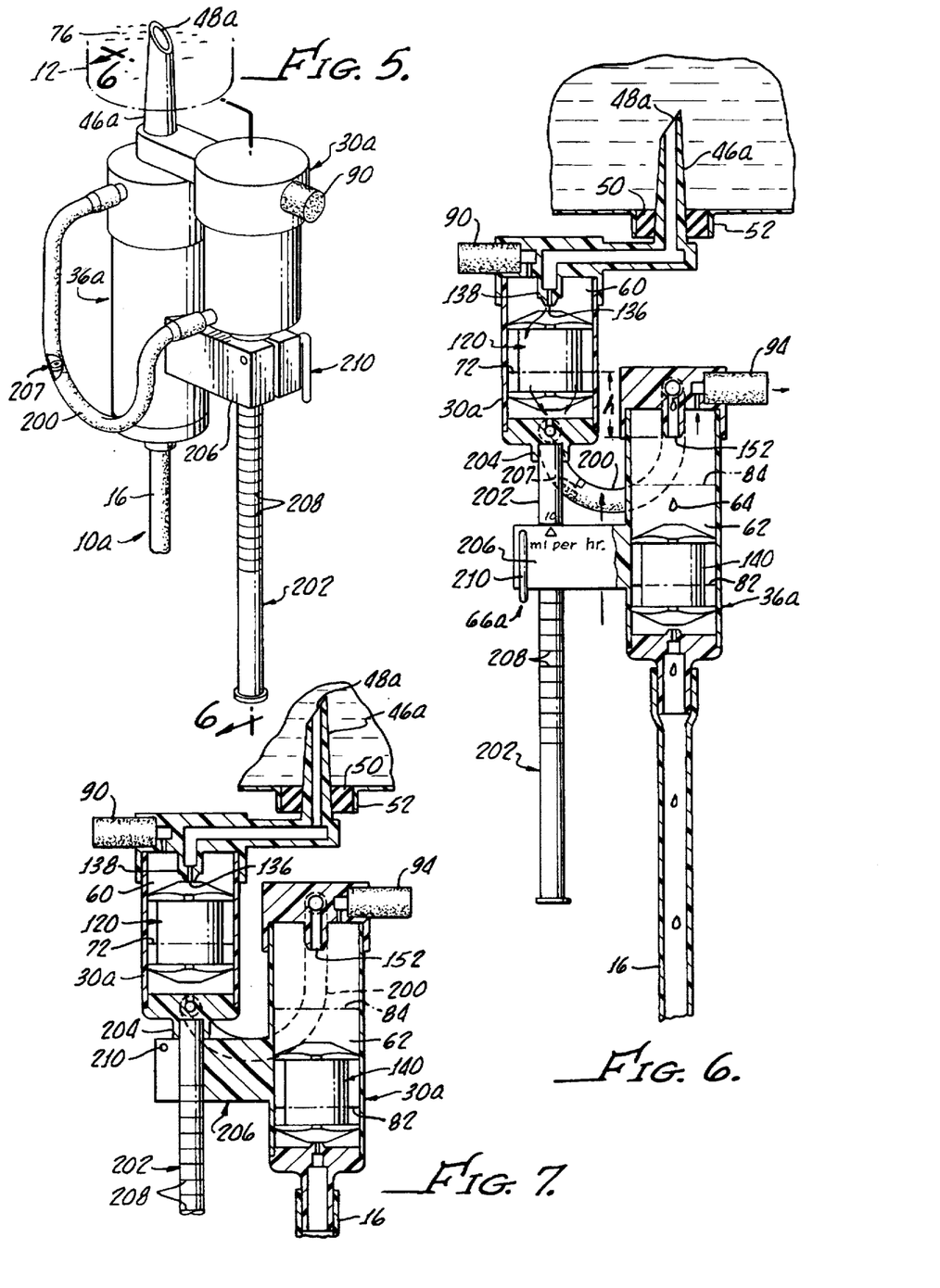
FIG. 5 is a perspective drawing of a variation, flow rate control device having first and second chambers which are vertically movable relative to one another for regulating the flow of fluid from a first chamber into a second, drip, chamber.
FIG. 6 is a longitudinal cross sectional view taken along line 6—6 of FIG. 5, showing the internal construction of the first variation device, including a first, upper, free-floating float valve and a second, lower, free-floating float valve for fluid flow through the device.
FIG. 7 is a partial cross sectional view similar to FIG. 6, showing the second chamber of the variation device elevated to a maximum-enabled position relative to first chamber.

Variation of FIGS. 5-7

A variation fluid flow control device 10a is depicted in FIGS. 5-7. In these FIGS. 5-7, elements and features of device 10a that are identical to those described above for device 10 are given the same reference numbers. Those elements and features of device 10a which are similar or equivalent to those elements and features described above for device 10 are given the same reference numbers followed by an "a." Entirely different elements and features of device 10a are given new reference numbers.

It is to be understood that although device 10a differs in external appearance from above-described device 10, its function and operation are similar except for the construction (described below) of flow regulating means 66a.

As shown in FIGS. 5-7, device 10a comprises a first, tubular upper shell segment 30a and a second, lower tubular shell segment 36a. Upper segment 30a is constructed to form an internal first chamber 60 having a first float valve 120 disposed therein. First chamber 60 is vented to atmosphere by a vent 90. Lower segment 36a is constructed to form a second chamber 62 having a second float valve 140 disposed therein. Second chamber 62 is vented to atmosphere through a vent 94.

A tapered, tubular spike 46a at the top of upper segment 30a is provided for penetrating through a seal 50 at a lower end 52 of a fluid source 12 (FIG. 6) to permit the gravity flow of fluid through an orifice 136 at the lower end of extension 138 into first chamber 60.

Respective upper and lower segments 30a and 36a of device 10a are constructed in substantially the same manner, and function in the same way, described above, as corresponding upper and lower segments 30 and 36 of device 10.

The principal difference between device 10a and device 10 is that the gravity flow of fluid from first chamber 60 of upper segment 30a into second chamber 62 of lower segment 36a is regulated by the relative vertical position between the upper and lower segments. To this end, a flexible fluid conduit 200 is connected between a lower region of upper segment 30a and an upper region of lower segment 36a (FIGS. 5 and 6).

Flow regulating means 66a comprises a vertical support member 202 which extends downwardly from tubular region 204 at the bottom of upper segment 30a. Vertically slidingly mounted over member 202 is a slide 206 which is connected to lower segment 36a so as to extend sidewardly therefrom (FIGS. 5-7).

The relative height between upper segment 30a and lower segment 36a can be easily adjusted, to regulate the flow of fluid from first chamber 60 into second. chamber 62, by sliding slide 206 (and consequently the lower segment)up or down support member 202. The effect of sliding lower segment 36a upwardly or downwardly on support member 202 actually varies the height, h, between fluid level 72 in first chamber 60 and fluid discharge opening 150 into second chamber 60.

A scale 208 may be engraved or other wise formed on support member 202 which is calibrated, for example, in milliliters per hour, to correspond to the precise fluid flow provided for various positions of slide 206 along the support member. As mentioned above, however, fluid flow rates can be verified by observing the drip rate of fluid through second chamber 62 (that is, by counting droplets 64 as they fall through the second chamber). Locking means 210, for example a clamp, are preferably provided for clamping slide 206 at any selected point along support member 202.

Operation of device 10a is otherwise the same as described above for device 10.

Although there have been described and illustrated a fluid flow control device (especially adapted for controlling the flow of IV fluid) and a variation thereof having a constant fluid head and variable flow control orifice or variable fluid head and a fixed size flow control orifice provision in accordance with the present invention for purposes of illustrating the manner in which the invention may be used to advantage, it is to be appreciated that the invention is not limited thereto. Therefore, any and all variations and modifications that may occur to those skilled in the applicable art are to be considered as being within the scope and spirit of the claims as appended hereto.

What is claimed is:

1. A gravity flow fluid flow device with constant fluid head provision, said device comprising:

a. a first, constant fluid head chamber having an upper fluid inlet end region and a lower, fluid outlet region;

b. a second, drip chamber having an upper fluid inlet end region and a lower, fluid outlet end region, said lower fluid outlet end region being configured for having attached thereto a conventional discharge tube;

c. fluid flow regulating means connected in fluid flow relationship between the fluid outlet end region of said first chamber and the fluid inlet end region of said second chamber for regulating the gravity flow of fluid from the first chamber into the second chamber; and d. means for enabling a fluid-flow connection between the fluid inlet end region of the first chamber and a lower, discharge region of a preexisting source of fluid that is open to ambient surrounding pressure through a collapsible container or a filtered vent; and e. fluid level control means disposed in said first chamber for causing, when said connecting means connects said first chamber to said preexisting source of fluid for receiving a flow of fluid therefrom, a preestablished fluid level to be substantially maintained in said first chamber as the fluid level in said connected source decreases, said fluid level control means including an orifice at the fluid inlet end region of said first chamber and a free-floating float valve disposed in said first chamber configured for blocking said orifice to stop a gravity flow of fluid through said orifice from said connected source when the fluid level in said first chamber is at said preestablished level and for floating downwardly and unblocking said orifice to permit a gravity flow of fluid through said orifice from said connected source when the fluid level in said first chamber falls below said preestablished level and until the fluid level returns to said preestablished level whereby said valve floats upwardly and again blocks off the flow of fluid through said orifice.

2. The gravity flow fluid flow device as claimed in claim 1, wherein said source of fluid is IV fluid.

3. The gravity flow fluid flow device as claimed in claim 1, wherein at least a side wall region of said second chamber is constructed of a transparent material so that a rate of fluid dripping through said second chamber can be observed.

4. The gravity flow fluid flow device as claimed in claim 1, including first venting means located at an upper region of said first chamber above said preestablished fluid level for venting the first chamber to ambient surrounding pressure.

5. The gravity flow fluid flow device as claimed in claim 1, including second venting means located at an upper region of said second chamber for venting the second chamber to ambient surrounding pressure.

6. The gravity flow fluid flow device as claimed in claim 1, wherein said fluid flow regulating means comprise a valve body having a rotatably-mounted valve stem for incremental rotational movement between a first, fully-closed position which blocks the gravity flow of fluid from the first chamber into the second chamber and a second, fully-open position in which the gravity flow of fluid from the first chamber into the second chamber is at a maximum flow.

7. The gravity flow fluid flow device as claimed in claim 6, wherein said valve stem is disposed in said valve body for being manually set at any selected rotational position between said first and second positions so as to thereby enable a user to selectively control the gravity flow of fluid from said first chamber into said second chamber.

8. The gravity flow IV fluid flow device as claimed in claim 7, including an indicator calibrated with respect to rotational positions of said valve stem for enabling a user to read fluid flow rates from the first chamber into the second chamber associated with different rotational positions of said valve stem.

9. The gravity flow IV fluid flow device as claimed in claim 1, wherein said fluid flow regulating means comprise a flexible fluid conduit connected in fluid flow relationship between the outlet end region of the first chamber and the fluid inlet end region of the second chamber.

10. The gravity flow fluid flow device as claimed in claim 9, wherein said fluid flow regulating means further comprise means for selectively controlling the vertical distance between said first chamber and said second chamber.

11. The gravity flow fluid flow device as claimed in claim 1, including means disposed in said second chamber for closing said lower, fluid outlet end region when no fluid is gravity flowing through and out thereof.

12. The gravity flow fluid flow device as claimed in claim 11, wherein said closing means include a float valve having a closure region which closes a fluid discharge opening in said lower, fluid discharge outlet end region when the fluid level in the second chamber is below a preestablished lower level and closes a fluid inlet opening into the second chamber when the fluid level in the second chamber reaches preestablished upper level.

13. A gravity flow IV fluid flow device with constant fluid head provision, said device comprising:
 a. a first chamber having an upper fluid inlet end region having a fluid flow orifice and a lower, fluid outlet region;
 b. means for enabling a fluid flow connection between the fluid inlet end region of the first chamber and a lower, discharge region of a preexisting, closed source of IV fluid so as to enable the gravity flow of fluid from said source through said fluid flow orifice into said first chamber;
 c. float valve means disposed in said first chamber for blocking said fluid flow orifice to stop the gravity flow of fluid from a connected source of IV fluid into the first chamber through said fluid flow orifice when the fluid level in said first chamber is at a preestablished fluid level and for unblocking said orifice to permit the gravity flow of fluid from said connected source of IV fluid through said fluid flow orifice whenever the fluid level in said first chamber is lower than said preestablished fluid level, said float valve means including a float valve constructed for freely floating up and down in said first chamber in response to changing fluid levels in said first chamber;
 d. a second, drip chamber having an upper fluid inlet end region and a lower, fluid outlet end region, said lower fluid outlet end region being configured for having attached thereto a conventional IV tube for providing fluid into a patient's body; and
 e. fluid flow regulating means connected in fluid flow relationship between the fluid outlet end region of said first chamber and the fluid inlet end region of said second chamber for regulating the gravity flow of fluid from the first chamber into the second chamber.

14. The gravity flow IV fluid flow device as claimed in claim 13, wherein at least a side wall region of said second chamber is constructed of a transparent material so that a rate of fluid dripping through said second chamber can be observed.

15. The gravity flow IV fluid flow device as claimed in claim 13, including first venting means located at an upper region of said first chamber above said preestablished fluid level for venting the first chamber to ambient surrounding pressure and second venting means located at an upper region of said second chamber for venting the second chamber to ambient surrounding pressure.

16. The gravity flow IV fluid flow device as claimed in claim 13, wherein said fluid flow regulating means comprise a valve body having a rotatably-mounted valve stem for incremental rotational movement between a first, fully-closed position which blocks the gravity flow of fluid from the first chamber into the second chamber and a second, fully-open position in which the gravity flow of fluid from the first chamber into the second chamber is at a maximum flow, said valve stem being disposed in said valve body for being manually set at any selected rotational position between said first and second positions so as to thereby enable a user to selectively control the gravity flow of fluid from said first chamber into said second chamber.

17. The gravity flow IV fluid flow device as claimed in claim 16, including an indicator calibrated with respect to rotational positions of said valve stem for enabling a user to read fluid flow rates from the first chamber into the second chamber associated with different rotational positions of said valve stem.

18. The gravity flow IV fluid flow device as claimed in claim 13, wherein said fluid flow regulating means comprise a flexible fluid conduit connected in fluid flow relationship between the outlet end region of the first chamber and the fluid inlet end region of the second chamber and means for selectively controlling the vertical distance between said preestablished fluid level in said first chamber and the fluid inlet region of the second chamber.

19. The gravity flow IV fluid flow device as claimed in claim 13, including means disposed in said second chamber for closing a fluid discharge opening in said lower, fluid discharge outlet end region when the fluid level in the second chamber is below a preestablished lower level and closing a fluid inlet opening into the second chamber when the fluid level in the second chamber reaches a preestablished upper level.

20. A gravity flow IV fluid flow device with constant fluid head provision, said device comprising:
 a. a first chamber having an upper fluid inlet end region having a fluid flow orifice and a lower, fluid outlet region;
 b. means for enabling a fluid flow connection between the fluid inlet end region of the first chamber and a lower, discharge region of a preexisting, closed source of IV fluid so as to enable the gravity flow of fluid from said source through said fluid flow orifice into said first chamber;
 c. a free-floating float valve disposed in said first chamber for blocking said fluid flow orifice to stop the gravity flow of fluid from a connected source of IV fluid into the first chamber through said fluid flow orifice when the fluid level in said first chamber is at a preestablished fluid level and for unblocking said orifice to permit the gravity flow of fluid from said connected source of IV fluid through said fluid flow orifice whenever the fluid level in said first chamber is lower than said preestablished fluid level;

d. a second, drip chamber having an upper fluid inlet end region and a lower, fluid outlet end region, said lower fluid outlet end region being configured for having attached thereto a conventional IV tube for providing fluid into a patient's body; and e. fluid flow regulating means connected in fluid flow relationship between the fluid outlet end region of said first chamber and the fluid inlet end region of said second chamber for regulating the gravity flow of fluid from the first chamber into the second chamber, said flow regulating means comprising a valve body having a rotatably-mounted valve stem for incremental rotational movement between a first, fully-closed position which blocks the gravity flow of fluid from the first chamber into the second chamber and a second, fully-open position in which the gravity flow of fluid from the first chamber into the second chamber is at a maximum flow, said valve stem being disposed in said valve body for being manually set at any selected rotational position between said first and second positions so as to thereby enable a user to selectively control the gravity flow of fluid from said first chamber into said second chamber.

21. The gravity flow IV fluid flow device as claimed in claim 20, wherein at least a side wall region of said second chamber is constructed of a transparent material so that a rate of fluid dripping through said second chamber can be observed.

22. The gravity flow IV fluid flow device as claimed in claim 20, including first venting means located at an upper region of said first chamber above said preestablished fluid level for venting the first chamber to ambient surrounding pressure and second venting means located at an upper region of said second chamber for venting the second chamber to ambient surrounding pressure.

23. The gravity flow IV fluid flow device as claimed in claim 20, including an indicator calibrated with respect to rotational positions of said valve stem for enabling a user to read fluid flow rates from the first chamber into the second chamber associated with different rotational positions of said valve stem.

24. The gravity flow IV fluid flow device as claimed in claim 20, including a second, free-floating float valve disposed in said second chamber for closing a fluid discharge opening in said lower, fluid discharge outlet end region when the fluid level in the second chamber is below a preestablished lower level and closing a fluid inlet opening into the second chamber when the fluid level in the second chamber reaches a preestablished upper level.

25. A gravity flow IV fluid flow device with variable fluid head provision, said device comprising:

a. a first chamber having an upper fluid inlet end region having a fluid flow orifice and a lower, fluid outlet region;

b. means for enabling a fluid flow connection between the fluid inlet end region of the first chamber and a lower, discharge region of a preexisting, closed source of IV fluid so as to enable the gravity flow of fluid from said source through said fluid flow orifice into said first chamber;

c. a free-floating ,float valve disposed in said first chamber for blocking said fluid flow orifice to stop the gravity flow of fluid from a connected source of IV fluid into the first chamber through said fluid flow orifice when the fluid level in said first chamber is at a preestablished fluid level and for unblocking said orifice to permit the gravity flow of fluid from said connected source of IV fluid through said fluid flow orifice whenever the fluid level in said first chamber is lower than said preestablished fluid level;

d. a second, drip chamber having an upper fluid inlet end region and a lower, fluid outlet end region, said lower fluid outlet end region being configured for having attached thereto a conventional IV tube for providing fluid into a patient's body; and e. fluid flow regulating means connected in fluid flow relationship between the fluid outlet end region of said first chamber and the fluid inlet end region of said second chamber for regulating the gravity flow of fluid from the first chamber into the second chamber, said fluid flow regulating means comprising a flexible fluid conduit connected in fluid flow relationship between the outlet end region of the first chamber and the fluid inlet end region of the second chamber with a fixed orifice therein and means for selectively controlling the vertical distance between said preestablished fluid level in said first chamber and the fluid inlet region of the second chamber.

26. The gravity flow IV fluid flow device as claimed in claim 25, wherein at least a side wall region of said second chamber is constructed of a transparent material so that a rate of fluid dripping through said second chamber can be observed.

27. The gravity flow IV fluid flow device as claimed in claim 25, including first venting means located at an upper region of said first chamber above said preestablished fluid level for venting the first chamber to ambient surrounding pressure and second venting means located at an upper region of said second chamber for venting the second chamber to ambient surrounding pressure.

28. The gravity flow IV fluid flow device as claimed in claim 25, including a second free-floating float valve disposed in said second chamber for closing a fluid discharge opening in said lower, fluid discharge outlet end region when the fluid level in the second chamber is below a preestablished lower level and closing a fluid inlet opening into the second chamber when the fluid level in the second chamber reaches a preestablished upper level.

* * * * *